US00PP13705P39

(12) United States Plant Patent
South

(10) Patent No.: US PP13,705 P3
(45) Date of Patent: Apr. 1, 2003

(54) DIANELLA PLANT NAMED 'SOUGOLD'

(75) Inventor: Darryl J. South, Lambells Lagoon (AU)

(73) Assignee: Darwin Plant Wholesalers, Winnellie (AU)

( * ) Notice: Subject to any disclaimer, the term of this patent is extended or adjusted under 35 U.S.C. 154(b) by 0 days.

(21) Appl. No.: 09/851,687

(22) Filed: May 8, 2001

(65) Prior Publication Data

US 2002/0170099 P1 Nov. 14, 2002

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—Fulwider, Patton, Lee & Utecht, LLP

(57) ABSTRACT

The claimed cultivar brings a new color to the 'SOUGOLD' series of dianellas and is characterized by a variegated leaf pattern having multiple linear longitudinal bands with green and gold coloring.

1 Drawing Sheet

1

BACKGROUND OF THE NEW PLANT

The present invention comprises a new and distinct cultivar of *Dianella ensifolia* known by the varietal name 'SOUGOLD' (Darwin Plant Wholesalers, plant breeder's identification number DIA 1) The new variety was discovered in a selective breeding program by Darryl J. South at Darwin, Australia, 13 Alphatonia Road, Lambell's Lagoon, Northern Territory. The new variety is a selection from the crossing of a "Green" form (unpatented) of dianella having no variegated striping and a "Variegated" form (unpatented) of dianella having green/white variegated material with further selection and vegetative propagation isolating green/gold variegated material. The selection criteria being gold and green variegated leaves.

The new variety is the result of a selective breeding program taken from off types noted in the Nursery at Lambell's Lagoon in July 1986. These off types were selected and propagated vegetatively, with further selections being made over four (4) generations selecting for differences in variation and green/gold leaf colors.

The new cultivar was first asexually reproduced by divisions at Darwin Plant Wholesalers located at Winnellie, in Northern Territory, Australia, P.O. Box 39196, Winnellie, Northern Territory 0821 and has been repeatedly asexually reproduced by divisions at Darwin Plant Wholesalers. Continued observations from the vegetative divisions have confirmed that the distinguishing features of this new cultivar came true, remain stable and are retained through successive propagation.

The new cultivar was grown outdoors under light shade cloth (approximately 50%), propagated from rhizomes with leaves, planted into 150 mm pots filled with regular standard potting mix, and nutrition maintained with slow release fertilizer. Pest and disease treatments were applied as required. Low pressure overhead irrigation was used. The plant exhibited 6 month response time from the rooted cutting to a flowering plant.

DESCRIPTION OF THE DRAWING

The accompanying drawing illustrates the new cultivar, the color being as nearly true as possible with color illustrations of this type.

2

DESCRIPTION OF THE NEW PLANT

The following detailed description sets forth characteristics of the new cultivar. The data which defines each characteristic was collected from asexual reproductions grown outdoors at Winnellie, in Northern Territory, Australia between October 1999 and February 2000. The plant histories were taken on rooted divisions believed to have been potted in a 150 cm pot on approximately October 1999 and flowering on approximately March 2000, outdoors and color readings were taken in daylight using The Royal Horticultural Society of London Colour Chart, 1986 Edition.

THE PLANT

Classification:

*Botanical.*—*Dianella ensifolia.*
*Commercial.*—'SOUGOLD'.
*Parentage.*—Naturally occurring sport or mutation of the species *Dianella ensifolia.*
*Origin.*—Mutation.
*Propagation.*—Rhizome separation.
*Rooting habit.*—Rhizomes are creeping and fibrous.

Form:

Upright perennial herb with horizontal subterranean rhizomes forming tight colonies with numerous erect narrow leaves as a terminal rosette.

*Height.*—Up to 700 mm.
*Growth.*—Tight colonies.
*Strength.*—Strong and upright.

Foliage: Terminal Rosette

Leaves: Leaves are tightly sheathed with a strongly isobilateral lower part and prominently keeled with no distinct inflection point; keel is finely serrated.

*Size.*—Length: approximately 560 mm mean for mature
Width: approximately 30 mm mean for mature
Length/Width ratio 17.96.
*Shape.*—Linear lanceolate.
*Margin.*—Entire.
*Texture.*—Smooth top and underside.

*Color.*—Top: Longitudinal parallel green and green-yellow striping of irregular widths with the color uniform along the leaf length; green striping is Green Group RHS 139A; yellow-green striping is Yellow-Green Group RHS 153B yellow stripe is Yellow Group RHS 8B. Underside: Green stripe is Yellow-Green Group RHS 137A. Yellow Green stripe is Yellow-Green Group RHS 153C and Yellow stripe is from Yellow Group RHS 8A.

Stem: Usually absent, basal leaves only

INFLORESCENCE

Blooming habit: Does not exceed leaf height

Borne: Inflorescence a panicle — florets on pedicel and pedicel on peduncle

Closed Florets:

*Form.*—Ovate.

*Color.*—Violet-Blue Group RHS 97A and 96A.

*Size.*—5–7 mm, 3 mm wide at widest point.

Open Florets:

*Form.*—6 petals, star-shaped.

*Color.*—Violet-Blue Group RHS 97A and 97B. Bright blue to purple perianth segments. Anther filament bases: Yellow Group RHS 5A with darker Yellow RHS 9A on also present.

*Size.*—Floret diameter 14–16 mm.

Petals:

*Quantity.*—6.

*Length.*—7–8 mm measured from the peduncle.

*Width.*—1.5–2.0 mm wide at widest point.

*Color.*—Violet-Blue Group RHS 97A and 97B.

Pedicel:

*Length.*—5–9 mm.

*Diameter.*—0.5–0.7 mm.

*Color.*—Yellow-Green Group RHS 144A.

Peduncle:

*Length.*—20–35 mm.

*Diameter.*—1 mm.

*Color.*—Yellow-Green Group RHS 144A.

Persistence:

*Disease resistance.*—No known specific disease resistance.

*Lasting quality.*—Flowers last approximately 1 day, generally not fully open before mid-morning.

Stamens:

*Anthers.*—Quantity: 6 Length: 1 mm.

*Filaments.*—Length: 3–4 mm.

*Color.*—Yellow Group RHS 5A with darker yellow RHS 9A also present.

Pistils:

*Stigma.*—Color: Translucent.

*Style.*—Length: 4–5 mm.

Fruit: Succulent berry.

*Color.*—Immature — Violet-Blue Group RHS 93C and 92A and 91A Mature — Violet-Blue Group RHS 94B and 94A.

*Seeds.*—Color — Black, shining, smooth surface texture Length: 3–6 mm.

GENERAL CHARACTERISTICS

'SOUGOLD' brings a new and distinct color to the Dianella series of plant. More specifically 'SOUGOLD' takes the form of an upright perennial herb with horizontal subterranean rhizomes forming tight colonies with numerous erect narrow leaves as a terminal rosette and introduces a variegated strongly isobilateral leaf base and leaf pattern with multiple linear longitudinal bands exhibiting alternating green and gold coloring on a flat linear lanceolate shaped leaf. At maturity 'SOUGOLD' has approximately 10–16 groups of 5 florets per inflorescence.

I claim:

1. A new and distinct variety of Dianella plant, substantially as shown and described.

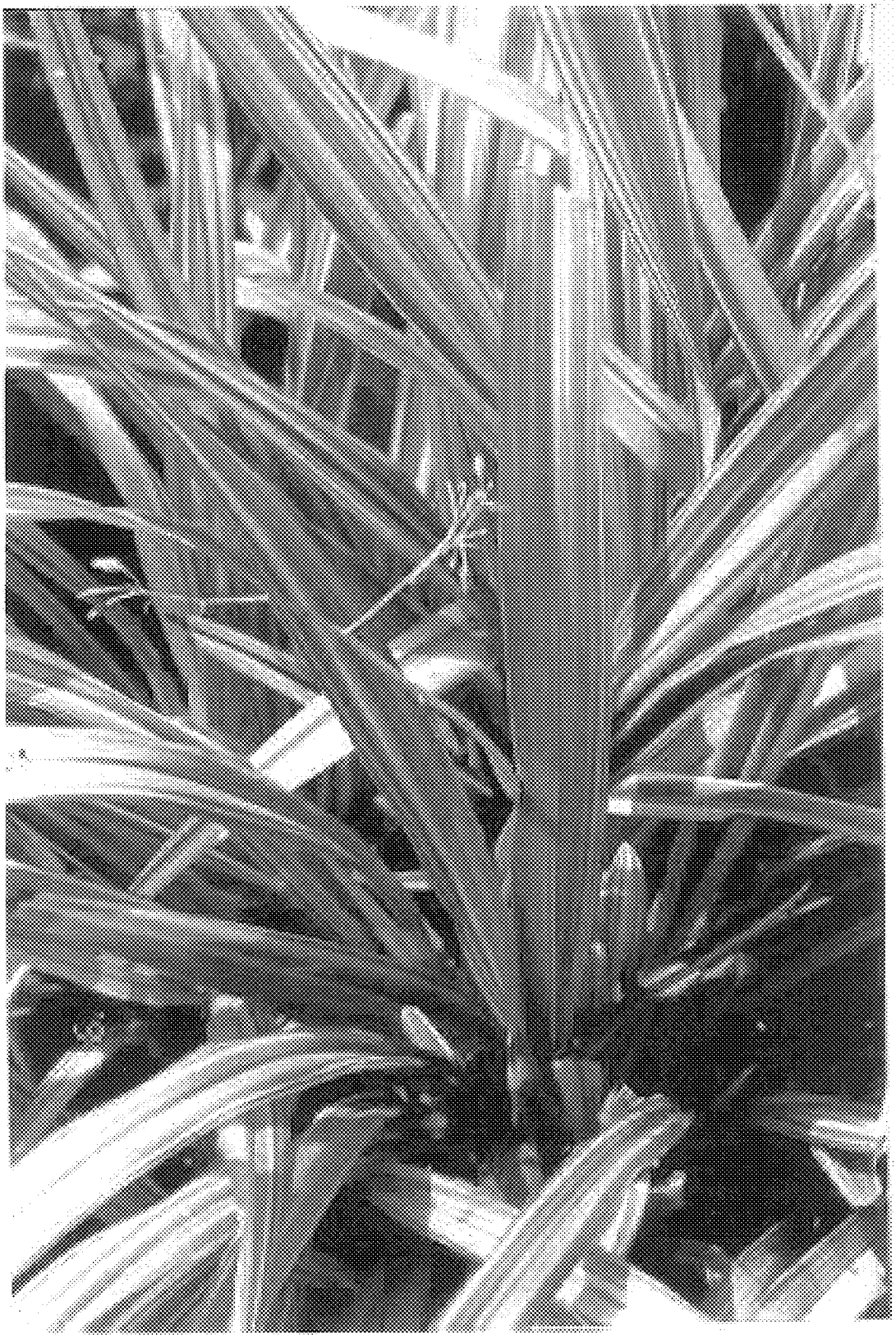

* * * * *